(12) United States Patent
Ramappa

(10) Patent No.: US 6,812,050 B1
(45) Date of Patent: Nov. 2, 2004

(54) SYSTEM AND METHOD OF EVALUATING GATE OXIDE INTEGRITY FOR SEMICONDUCTOR MICROCHIPS

(75) Inventor: Deepak A. Ramappa, Dallas, TX (US)

(73) Assignee: Texas Instruments Incorporated, Dallas, TX (US)

(*) Notice: Subject to any disclaimer, the term of this patent is extended or adjusted under 35 U.S.C. 154(b) by 0 days.

(21) Appl. No.: 10/463,022

(22) Filed: Jun. 13, 2003

(51) Int. Cl.[7] ................ H01L 21/00; G01N 27/60
(52) U.S. Cl. .................... 438/17; 324/71.1
(58) Field of Search ................ 324/71.1, 751, 324/501; 702/170, 172; 438/14, 16–18

(56) References Cited

U.S. PATENT DOCUMENTS

| | | | | |
|---|---|---|---|---|
| 5,391,502 A | * | 2/1995 | Wei ................ | 438/466 |
| 6,091,249 A | * | 7/2000 | Talbot et al. ........ | 324/751 |
| 6,573,736 B1 | * | 6/2003 | Lee et al. .......... | 324/751 |

FOREIGN PATENT DOCUMENTS

| | | | | |
|---|---|---|---|---|
| JP | 2003066118 A | * | 3/2003 | G01R/31/302 |

OTHER PUBLICATIONS

Cappel et al., "The Advantages of In–Line Electron–Beam Wafer Inspection," Summer 2000, Yield Management Solutions, pp. 8–12.*

Liang et al., "Rapid in–line characterization of plasma–induced damage on a 0.25 um CMOS ASIC technology," Jun. 1998, 3rd International Symposium on Plasma Process–Induced Damage, 1998, pp. 148–151.*

Colvin, "A New Technique to rapidly Identify Gate Oxide leakage in Field Effect Semiconductors Using a Scanning Electron Microscope," 1990, EOS/ESD Syposium Proceedings, pp. 173–176.*

* cited by examiner

*Primary Examiner*—Evan Pert
(74) *Attorney, Agent, or Firm*—Yingsheng Tung; Wade James Brady, III; Frederick J. Telecky, Jr.

(57) ABSTRACT

The present invention provides a system and method for evaluating gate oxide integrity in a semiconductor wafer. The system may include: a semiconductor wafer; a layer of gate oxide on the semiconductor wafer; a layer of polysilicon on the gate oxide; an electron beam microscope with adjustable energy levels, wherein the electron beam is directed at the semiconductor wafer; an electron beam inspection tool used to detect passive voltage contrasts within the gate oxide layer. The system may also include a measuring tool for measuring an electrical current level of the semiconductor substrate. The system may also include an electrical ground connected to the semiconductor wafer. The system may also include the energy levels vary from about 600 eV to 5000 eV.

11 Claims, 3 Drawing Sheets

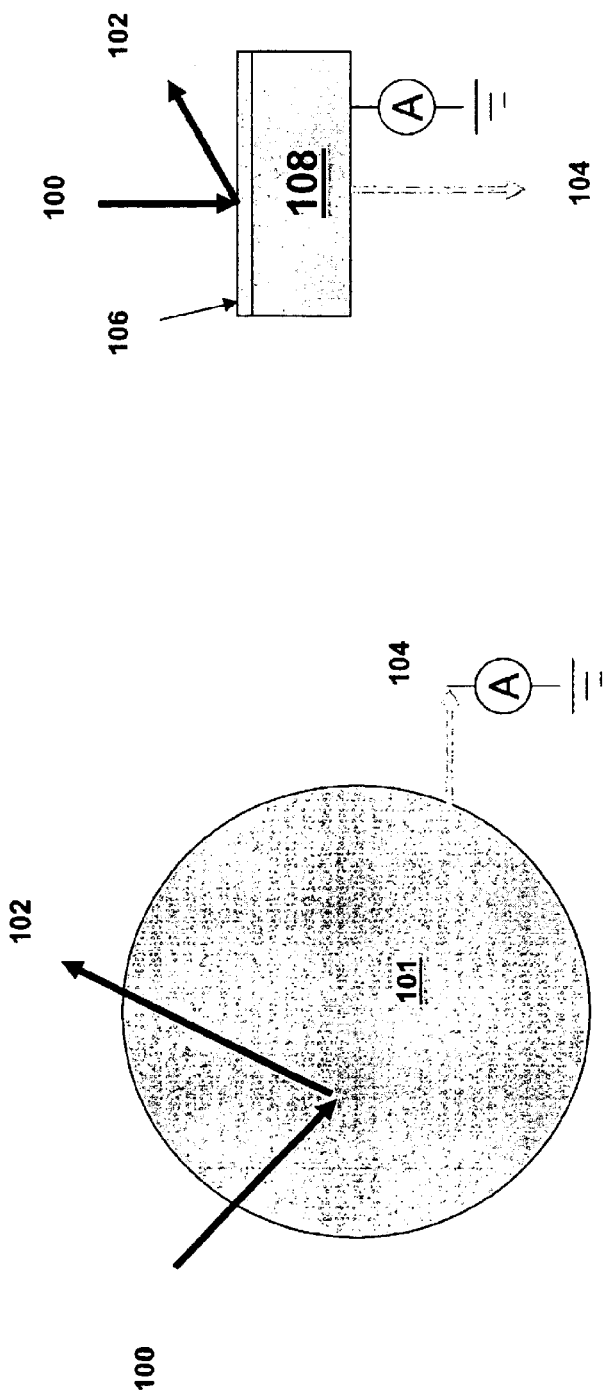

SYSTEM AND METHOD OF EVALUATING GATE OXIDE INTEGRITY FOR SEMICONDUCTOR MICROCHIPS

BACKGROUND OF THE INVENTION

The present invention relates generally to semiconductor electronic circuits and, more particularly, to a system and method for evaluating gate oxide integrity for semiconductor microchips.

Gate oxide integrity (GOI) is a critical metric for the effective functioning of the transistor. With scaling of devices the gate oxides have become thinner to the extent that present day devices use oxides on the range 12–24 Angstroms. This makes them more susceptible to defects which are detrimental to eventual yield of the devices, Defects cause enhanced leakage and eventually premature (non-intrinsic) breakdown of oxides. The GOI integrity needs to be evaluated early in the device processing in the front end of the line to prevent unnecessary, wasteful utilization of time and resources in the back end of the line (BEOL). Present methods use an in-line invasive probe on a few sampled sites to determine current-voltage characteristics and from it to assess gate oxide quality or health.

Currently, there is not a good non-contact system or method to test gate oxide integrity during the semiconductor microchip manufacture itself. All existing methods use probes to test the gate oxide integrity after the semiconductor processing is completed (End of line). In addition, the probes or methods used in the current test systems can introduce contamination on the semiconductor wafers. Moreover, the testing systems only test a small set of specific sites on the semiconductor wafer. Thus they do not provide any wafer-spatial signature information. Active feedback of any spatial yield loss because of gate oxide integrity degradation is critical. Lack thereof results in continued faulty processing.

Therefore, what is needed, is a non-invasive system and method that tests gate oxide integrity, in-line amidst the different semiconductor processes. The method also needs to be fast, efficient, with more wafer spatial signature information, in order to provide active feedback and thus control process excursions and thus reduce yield loss.

SUMMARY OF THE INVENTION

The present disclosure provides a system and method that provides an improved method of inline evaluation of gate oxide integrity using electron beams.

The present invention provides a system and method for evaluating gate oxide integrity using electronic elements in a semiconductor wafer. The system may include: a semiconductor substrate on the semiconductor wafer; a layer of gate oxide on the semiconductor substrate; a layer of polysilicon on the gate oxide; an electron beam microscope with adjustable energy levels, wherein the electron beam microscope is directed at the semiconductor wafer; an electron beam inspection tool used to detect contrasts within the gate oxide layer. The system may also include a measuring tool for measuring an electrical current level of the semiconductor substrate. The system may also include an electrical ground connected to the semiconductor wafer. The system may also include the electron beam energy levels vary from about 600 volts to 5000 volts.

Therefore, in accordance with the previous summary, objects, features and advantages of the present disclosure will become apparent to one skilled in the art from the subsequent description and the appended claims taken in conjunction with the accompanying drawings.

BRIEF DESCRIPTION OF THE DRAWINGS

FIG. 2 is a diagram of a semiconductor wafer under inspection by the preferred embodiment;

FIG. 3 is a diagram of element within a semiconductor wafer under inspection of the preferred embodiment.

DETAILED DESCRIPTION OF THE PREFERRED EMBODIMENTS

The present disclosure can be described by the embodiments given below. It is understood, however, that the embodiments below are not necessarily limitations to the present disclosure, but are used to describe a typical implementation of the invention.

Gate oxide integrity (GOI) is a critical metric for effective functioning of transistors on the semiconductor wafers. In addition, since scaling has reduced the gate oxide thickness to less than 20 Angstroms, the gate oxide integrity is more susceptible to defects and failure. Moreover, it is now even more critical to evaluate spatial gate-oxide yield in-line in order to save subsequent processing costs, resources and product loss.

Gate oxide integrity is degraded by many factors. A few of these are: metal precipitates; interface roughness; stacking faults; crystal originated pits; plasma induced damage; and impurities introduced during cleaning the wafer prior to forming the gate oxide. Catastrophic breakdown in gate oxide is directly indicated by complete opens due to breakdown that may be caused by metal precipitates, stacking faults, or crystal originated pits. A soft breakdown is indicated by an increase in oxide leakage with the oxide dielectric quality degradation which is usually stress induced (plasma damage).

The present invention is a non-contact method of evaluating gate oxide integrity. Because the method is non-contact, inadvertent contamination and damage is minimized on the product wafers that are inspected. In addition, this non-contact method can be used to inspect a greater number of sites per wafer, thus giving a spatial indication of the probable cause of certain regions of the wafer having bad GOI. In this embodiment, about 200 sites could be inspected per minute. Thus this method also provides information as to the possible sources of yield degrading mechanisms at the gate and pre-gate level.

Figure 1:
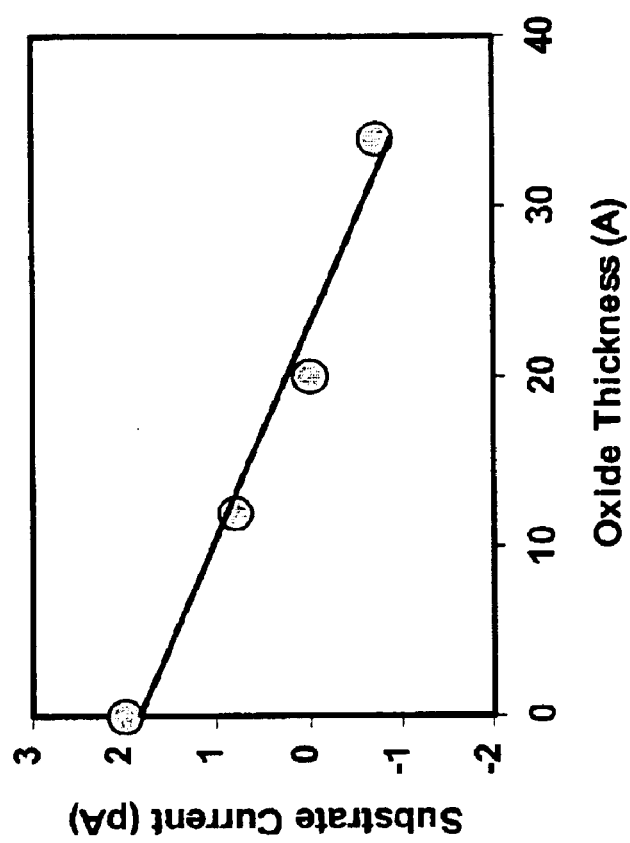
FIG. 1 is a mapping of substrate current vs. oxide thickness

It has been found that a correlation exists between the electron-beam induced substrate current and gate oxide thickness. An example of the correlation between substrate current and gate oxide thickness is shown in FIG. 1.

Electron-beam (e-beam) tools like the Secondary Electron Microscopes (SEM) and E-beam inspection tools like eS20 (Registered TM of KLA-Tencor Corporation) are regularly used for imaging defects (SEM) and detecting passive voltage contrast (eS20). The tools employ an electron beam with adjustable beam energies. Now referring to FIGS. 2 and 3, the e-beam 100, when incident on a wafer 101, induces secondary electrons 102 which are produced due to interaction of e-beam electrons with the surface atoms of the wafer, including the gate oxide 106 on top of a silicon wafer substrate 108. The emitted secondary electrons 102 are then captured by a secondary electron detector (not shown) to image the wafer 101 surface. A ground path that leads to the surface of wafer 101 conducts electrons away from the wafer surface as shown in the general direction by arrow 104.

Figure 4:
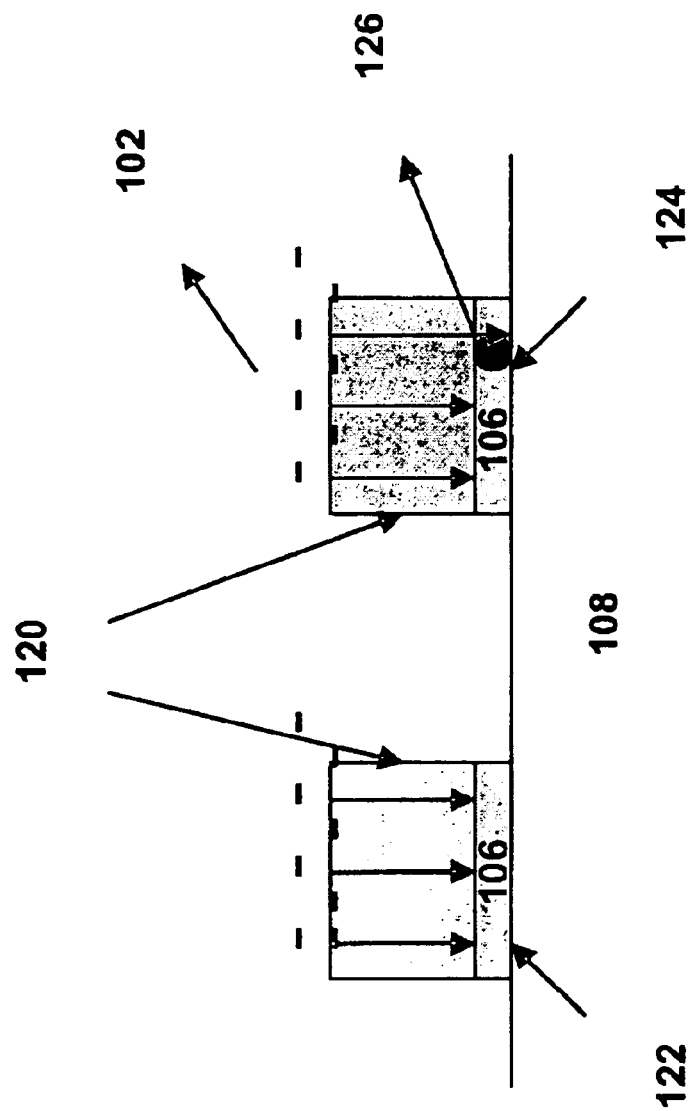
FIG. 4 is a diagram illustrating an example of a good gate oxide and an example of a bad gate oxide.

Now turning to FIG. 4, another example routinely encountered in semiconductor manufacturing is shown to help illustrate the invention. Two gates are shown with poly layers 120 and oxide layers 106 on top of the silicon 108. In addition, a dark feature 126 is shown which represents a defect or anomaly in the oxide which degrades the oxide quality and causes the oxide to leak instead of insulate. As shown, gate 124 is compromised while gate 122 appears to have no defects. Gate 124 appears dark to the secondary electron detector as those types of features 126 conduct electrons away from the surface.

In addition, poly features 120 which are not grounded or have a presence of an insulating dielectric 106 between them and the wafer substrate 108, result in charge accumulation on the surface. The charge accumulation builds up an electrical field across the dielectric oxide. These features appear bright to the secondary electron detector as the surface accumulates charge. These bright and dark contrasts are termed 'passive voltage contrast'. A dark feature indicates catastrophic breakdown in the gate oxide integrity. SEM inspection tools like the eS20 can be programmed to detect such voltage contrast differences. For thin gate oxides, such an electrical field resulting from incident e-beams will stress the oxide and induce a 'stress induced leakage current' (SILC). SILC is analogous to current voltage characteristics obtained at the end of line on a finished product probe yield. With increasing electrical fields, the dielectric eventually breaks down and bleeds charge to the wafer substrate. This is effectively gate oxide breakdown. The breakdown changes the charge density on the feature surface and its secondary electron scattering intensity changes from 'bright' to 'dark'. Essentially, gate oxides under poly features which are weaker will leak and breakdown at lower e-beam energies and lesser charge accumulation fields than more robust oxides. A soft breakdown can be detected as a relative increase in substrate current from nominal value for a known oxide thickness through the same methods. Thus, a tool like the eS20 can then be used to identify regions of weak oxides which change contrast for lower e-beam energies due to breakdown. This system and method can be implemented by succesively scanning the wafers to detect voltage contrast with successive ramped e-beam energies. In the one embodiment, substrate currents were measured for e-beams with increasing energies between 600 [v] eV and 5000 [v] eV. The charge needed to breakdown is used to extract a spatial GOI metric.

It is understood that several modifications, changes and substitutions are intended in the foregoing disclosure and in some instances some features of the invention will be employed without a corresponding use of other features. Accordingly, it is appropriate that the appended claims be construed broadly and in a manner consistent with the scope of the invention.

What is claimed is:

1. A method for evaluating gate oxide integrity within an electrical element in a semiconductor wafer, the method comprising:

providing a semiconductor wafer;

forming a gate oxide layer on the semiconductor wafer;

forming a polysilicon layer on the gate oxide layer;

directing an electron beam toward the semiconductor wafer;

using an electron beam inspection tool to measure contrasts within the gate oxide layer; and estimating and mapping a thickness of the gate oxide layer.

2. The method of claim 1 further including measuring an electrical current level of the semiconductor wafer.

3. The method of claim 1 further including connecting an electrical ground to the semiconductor wafer.

4. The method of claim 1 further including varying an energy level of the electron beam from about 600 eV to 5000 eV.

5. The method of claim 1 further including feeding back contrast information from the electron beam inspection tool.

6. The method of claim 1 wherein the gate oxide layer is in the range 0 to 100 Angstroms.

7. The method of claim 1 further including using the electron beam inspection tool to detect passive voltage contrasts within a gate structure.

8. A method for evaluating gate oxide integrity within a transistor in a semiconductor wafer, the method comprising:

providing a semiconductor wafer;

forming a gate oxide layer of 0 to 100 angstroms on the semiconductor wafer;

forming a polysilicon layer on the gate oxide layer;

directing an electron beam of variable energy toward the semiconductor wafer;

using an electron beam inspection tool to measure passive voltage contrasts within the gate oxide layer, and estimating and mapping a thickness of the gate oxide layer.

9. The method of claim 8 further including measuring an electrical current level of the semiconductor wafer according to grounded elements.

10. The method of claim 8 further including varying the energy level of the electron beam from about 600 eV to 5000 eV.

11. The method of claim 8 further including feeding back contrast information from the electron beam inspection tool.

* * * * *